United States Patent [19]
Rhim et al.

[11] Patent Number: 5,447,788
[45] Date of Patent: Sep. 5, 1995

[54] POROUS, NONWOVEN LIQUID-ACTIVATED BARRIER

[75] Inventors: Hannong Rhim, Roswell; Eugenio G. Varona; Lin-Sun Woon, both of Marietta, all of Ga.

[73] Assignee: Kimberly Clark Corporation, Neenah, Wis.

[21] Appl. No.: 242,918

[22] Filed: May 16, 1994

[51] Int. Cl.⁶ .............................................. B32B 27/00
[52] U.S. Cl. ..................... 428/284; 428/221; 428/224; 428/286; 428/288; 428/296; 428/297; 428/298; 428/304.4; 428/308.4
[58] Field of Search ............... 428/224, 288, 297, 298, 428/286, 284, 296, 903, 304.4, 308.4, 221

[56] References Cited

U.S. PATENT DOCUMENTS

| | | | |
|---|---|---|---|
| 3,654,929 | 4/1972 | Nilsson et al. | 128/287 |
| 3,888,256 | 6/1975 | Studinger | 128/296 |
| 4,592,751 | 6/1986 | Gegelys | 604/368 |
| 4,846,813 | 7/1989 | Raley | 604/385.1 |
| 4,855,179 | 8/1989 | Bourland et al. | 428/296 |
| 5,016,952 | 5/1991 | Arroyo et al. | 350/96.20 |
| 5,213,881 | 5/1993 | Timmons et al. | 428/224 |
| 5,342,335 | 8/1994 | Rhim | 604/358 |

FOREIGN PATENT DOCUMENTS

0176316 4/1986 European Pat. Off. .

*Primary Examiner*—James J. Bell
*Attorney, Agent, or Firm*—William E. Maycock

[57] ABSTRACT

A porous, nonwoven liquid-activated barrier which includes a fibrous nonwoven web in which at least about 50 percent by weight of the fibers constituting the fibrous nonwoven web are prepared from a liquid-swellable polymer which is not significantly soluble in the liquid. In addition, the fibers of the fibrous nonwoven web have diameters in a range of from about 0.1 to about 100 micrometers. The pores of the fibrous nonwoven web have a longest dimension in a range of from about 0.3 to about 300 micrometers. In the presence of liquid, the fibers swell to an extent sufficient to substantially block the passage of liquid through the fibrous nonwoven web. In many instances, the liquid will be water.

28 Claims, 2 Drawing Sheets

POROUS, NONWOVEN LIQUID-ACTIVATED BARRIER

BACKGROUND OF THE INVENTION

The present invention relates to a barrier material which is impervious to water.

Nonwoven webs currently are employed in a variety of such disposable absorbent products as diapers; incontinent products; feminine care products, such as tampons and sanitary napkins; wipes; towels; sterilization wraps; medical drapes, such as surgical drapes and related items; medical garments, such as hospital gowns, shoe covers, and the like, to name but a few. The nonwoven webs can be utilized as a single layer or as a component of a multilayered laminate or composite. When a multilayered laminate or composite is present, often each layer is a nonwoven web. Such structures are useful for wipes, towels, industrial garments, medical garments, medical drapes, and the like.

Desired characteristics of such nonwoven webs frequently include permeability to air and water vapor (breathability), but impermeability to liquids. Perhaps the most common product exhibiting these characteristics is a laminate of three nonwoven webs, the outer layers being spunbonded webs and the inner layer being a meltblown web. Such a material is referred to in the art as an SMS laminate. The webs of which the laminate is composed typically are prepared from polyolefins, with polypropylene being the polymer of choice. While these laminates and similar materials have found widespread acceptance, there still is an opportunity for materials having an increased impermeability to water. For example, SMS laminates are porous in order to provide the desired breathability. However, liquids can penetrate through the fabric under certain circumstances, such as when the liquid is under pressure or pressure is applied to fabric to which liquid has been applied. While the inclusion of a film in the laminate will prevent passage of liquid, breathability can be either lost or significantly reduced.

SUMMARY OF THE INVENTION

In response to the discussed difficulties and problems encountered in the prior art, a new breathable barrier has been discovered which reacts to a liquid to prevent passage of liquid therethrough. Accordingly, the present invention provides a porous, nonwoven liquid-activated barrier which includes a porous, fibrous nonwoven web in which at least about 50 percent by weight of the fibers of which the fibrous nonwoven web is composed are prepared from a liquid-swellable polymer which is not significantly soluble in the liquid. The fibers have diameters in a range of from about 0.1 to about 100 micrometers and the pores of the fibrous nonwoven web have a longest dimension in a range of from about 0.3 to about 300 micrometers. In the presence of liquid, the fibers swell to an extent sufficient to substantially block the passage of liquid through the fibrous nonwoven web. In many instances, the liquid is water.

The present invention also provides a porous, nonwoven water-activated barrier which involves a multilayered nonwoven structure, at least one layer of which is the porous, fibrous nonwoven web described above. For example, the porous, fibrous nonwoven web may be incorporated into an SMS laminate adjacent to and contiguous with the meltblown nonwoven web component of the laminate.

DETAILED DESCRIPTION OF THE INVENTION

Figure 1:
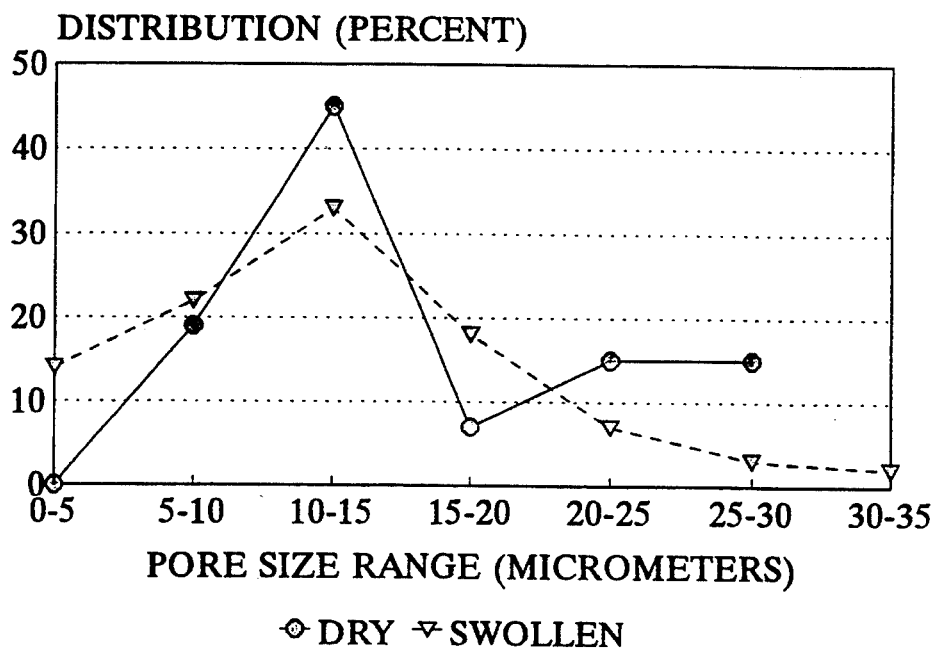
FIG. 1 is a plot of the pore size distribution of a porous, nonwoven liquid-activated barrier of the present invention before and after exposing the barrier to liquid, i.e., in a dry state and in a swollen condition.

As used herein, the term "liquid" is meant to include any liquid with which the porous, nonwoven liquid-activated barrier of the present invention may come in contact. The liquid of primary interest is water. The term "water" is used herein to encompass any aqueous medium, including, but not limited to, such aqueous bodily fluids as blood, urine, menses, and the like.

Because the liquid-activated barrier of the present invention is porous, it is breathable, i.e., permeable to the passage therethrough of gases, such as air and water vapor. In general, such barrier is a porous, fibrous nonwoven web in which at least about 50 percent by weight of the fibers constituting the fibrous nonwoven web are prepared from a liquid-swellable polymer which is not significantly soluble in the liquid. The fibers of the fibrous nonwoven web have diameters in a range of from about 0.1 to about 100 micrometers, and the pores of the fibrous nonwoven web have a longest dimension in a range of from about 0.3 to about 300 micrometers. Finally, in the presence of liquid, the fibers swell to an extent sufficient to substantially block the passage of liquid through the fibrous nonwoven web.

The term "fluid-activated barrier," therefore, is used herein to mean that the pores of the fibrous nonwoven web are capable of allowing the passage of a liquid therethrough, but that, upon exposure to the liquid, the fibers swell to an extent sufficient to substantially block the passage of liquid through the fibrous nonwoven web. In other words, the pores of the fibrous nonwoven web are large enough to permit the passage of liquid through the web. However, because of the presence of liquid-swellable fibers in the fibrous nonwoven web, such fibers swell to an extent which substantially closes the pores of the web, thereby substantially blocking the passage of liquid through the web.

As used herein, the term "is not significantly soluble in the liquid" means that the liquid does not dissolve an amount of the fibers sufficient to significantly adversely affect web integrity. That is, web integrity generally is maintained in the presence of the liquid. In certain embodiments, such as when the liquid-swellable polymer is a poly(vinyl alcohol) and the liquid is water, it is permissible for the fibers to be soluble in the liquid at temperatures outside the range of temperatures normally encountered during use of the product of which the barrier of the present invention is a component, e.g., temperatures greater than about 50° C. Stated differently, a range of temperatures normally encountered during use of many products of which the barrier of the present invention can be a component is from about ambient temperature to about 50° C.

In general, the liquid-swellable polymer can be any polymer which swells in the presence of a liquid of interest. Since the liquid of interest frequently will be water, the liquid-swellable polymer frequently will be a water-swellable polymer. Examples of water-swellable polymers include, by way of illustration only, poly(acrylic acid), poly(methacrylic acid), polyacrylamide, poly(N,N-dimethylacrylamide), poly(methylacrylamide), poly(vinyl alcohol), polyacrolein, poly(2-methoxyethoxyethylene), poly(3-morpholinoethylene), poly(N-1,2,4-triazolylethylene), poly[imino(1-oxotrimethylene)], poly(maleic anhydride), lower molecular weight phenol-formaldehyde resins, lower molecular weight urea-formaldehyde resins, cellulose acetate (lower degree of substitution polymers), gelatin, and the like. The water-swellable polymers may be crosslinked, heat-treated, or otherwise treated or modified to alter water-swellability and/or water-solubility characteristics. Desirably, the water-swellable polymer will be a poly(vinyl alcohol).

As already stated, the fibers of the fibrous nonwoven web have diameters in a range of from about 0.1 to about 100 micrometers, and the pores of the fibrous nonwoven web have a longest dimension in a range of from about 0.3 to about 300 micrometers. For example, the fibers can have diameters in a range of from about 0.5 to about 40 micrometers. As a further example, the pores can have a longest dimension in a range of from about 2 to about 100 micrometers.

Broadly stated, in the presence of liquid, the fibers swell to an extent sufficient to substantially block the passage of liquid through the fibrous nonwoven web. As used herein, fiber swelling refers to increases in fiber diameter. Thus, on the average, each fiber diameter ideally should increase by an amount at least equal to approximately one-half the size of each pore. Accordingly, larger pores generally require larger fibers, and for smaller pores, smaller fiber diameters often will suffice. Furthermore, pore closure efficiency is in part dependent upon pore size uniformity. The more uniform the pore sizes, the more effective will be the swelling process in the presence of liquid to close the pores.

Other factors affecting pore closure are the rate of fiber swelling and the degree to which the fibers swell. If the fibers swell too slowly, pore closure will not take place quickly enough to prevent the passage of liquid through the web. The same consequence will result if the fibers do not swell sufficiently, i.e., do not exhibit a sufficient increase in diameter to close substantially all of the pores in the area of liquid exposure. Thus, the selections of fiber diameters and pore sizes are, at least in part, dependent upon the fiber swelling rate and the degree of fiber swelling. Desirably, the fiber diameters will increase by at least about 50 percent upon exposure to liquid. That is, the diameter ratio desirably will increase to at least about 1.5. As used herein, the term "diameter ratio" (or "fiber diameter ratio") means the ratio of the fiber diameter after being exposed to a liquid for a given time to the original fiber diameter or the diameter of the fiber before exposure to liquid (sometimes referred to as $D/D_0$). More desirably, the diameter ratio of about 1.5 will be reached within about 10 seconds. Still more desirably, such diameter ratio will be reached within about 5 seconds.

In general, the porous, fibrous nonwoven web can be made by any process known to those having ordinary skill in the art. Such processes include, for example, meltblowing, coforming, spunbonding, hydroentangling, carding, air-laying, wet spinning, dry spinning, solution spinning, and wet-forming.

The present invention is further described by the examples which follow. Such examples, however, are not to be construed as limiting in any way either the spirit or the scope of the present invention. In the examples, all parts are by weight, unless stated otherwise.

Example 1

Preparation and Characterization of Fluid-Activated Barrier

The liquid-swellable polymer was a water-swellable poly(vinyl alcohol), Airvol® 125 (Air Products and Chemicals, Inc., Allentown, Pa.). The polymer was 99 percent hydrolyzed and had a medium molecular weight of about 80,000. The poly(vinyl alcohol) was dissolved in water at a solids content of about 30 percent by weight, based on the total weight of the solution. The solution also contained 10 percent by weight, based on the weight of poly(vinyl alcohol), of a poly(ethylene glycol), PEG-400 (Union Carbide Corporation), having a molecular weight of 400. Both molecular weights are understood to be weight-average molecular weights.

The poly(vinyl alcohol) solution was prepared by first placing 6,700 parts of a mixture of ice and water and 300 parts of PEG-400 in a ten-liter, oil-jacketed autoclave equipped with a stirrer and thermometer. The resulting mixture was stirred at 100-200 revolutions per minute (rpm) for a time sufficient to establish a vortex about the shaft of the stirrer. The poly(vinyl alcohol), 3,000 parts in the form of granules, then was slowly poured into the vortex to disperse the granules without clumping. The autoclave then was heated to about 82° C. and the stirrer speed was increased to about 700 rpm. The mixture was heated and stirred overnight. The solution then was deaerated by simply allowing it to stand for two to three hours without stirring. At the end of this time, the solution was clear and free of both undissolved particles of poly(vinyl alcohol) and air bubbles.

A porous, fibrous nonwoven web was formed by solution spinning the foregoing poly(vinyl alcohol) solution essentially as described in U.S. patent application Ser. No. 08/172,018, filed Dec. 22, 1993, now U.S. Pat. No. 5,342,335 which is incorporated herein by reference. The solution spinning apparatus utilized a six-inch (15.2-cm) wide die having 180 orifices in a single row running the length of the die (30 orifices per inch or about 11.8 orifices per cm). Each orifice had a diameter of 0.38 mm. Each opening for the primary gas was 2.8 mm and the primary gas was pure steam at a temperature of approximately 95°-105° C. and a pressure of 20-50 inches of water (0.05-0.13 kilograms per square cm). The secondary gas was compressed air heated to a temperature of about 204° C. Both the solution temperature and the die tip temperature were maintained at about 82° C. and the throughput or extrusion rate was 40 grams per minute. The autoclave was pressurized with compressed air at a pressure of about 100 pounds per square inch, gauge (psig, or about 7 kg per square cm) to ensure a sufficient inlet pressure for a Zenith metering pump which was connected to the autoclave via a drain valve. The resulting poly(vinyl alcohol) nonwoven web contained 10-20 percent by weight residual moisture, but felt dry and soft to the touch and had a fairly high web strength.

The porosity of the poly(vinyl alcohol) nonwoven web (PVOH web) before and after being exposed to water was measured by means of a Coulter Porometer. Also measured was the porosity of a standard polypropylene meltblown nonwoven web (MB web) of the type used to prepare the Control laminates described in Example 2. The poly(vinyl alcohol) nonwoven web in the dry state and the meltblown web each had a basis weight of 0.5 ounces per square yard (osy, about 17 grams per square meter or gsm). The results are summarized in Table 1 (in the table, "(a)" represents before exposure and "(b)" represents after exposure).

TABLE 1

Summary of Pore Size Distribution Measurements

| Web | Pore Size Distribution (Percent) | | | | | | |
|---|---|---|---|---|---|---|---|
| | 0–5μ | 5–10μ | 10–15μ | 15–20μ | 20–25μ | 25–30μ | 30–35μ |
| PVOH (a) | 0 | 19 | 45 | 7 | 15 | 15 | |
| PVOH (b) | 14 | 22 | 33 | 18 | 7 | 3 | 2 |
| MB | | 10 | 68 | 21 | 0.5 | 0.1 | |

The pore closing of the poly(vinyl alcohol) nonwoven web upon being exposed to water is evident from the data in Table 1. In order to better illustrate this pore closing effect, the data for the poly(vinyl alcohol) nonwoven web before and after exposure to water were plotted as pore size range versus percent distribution. The plots are shown in FIG. 1. The plot before exposure to water is identified in FIG. 1 as "Dry" and the plot after exposure is identified in the figure as "Swollen;" the pore-closing effect of the water on the web is clearly evident and applicable across the entire pore size range.

Figure 2:
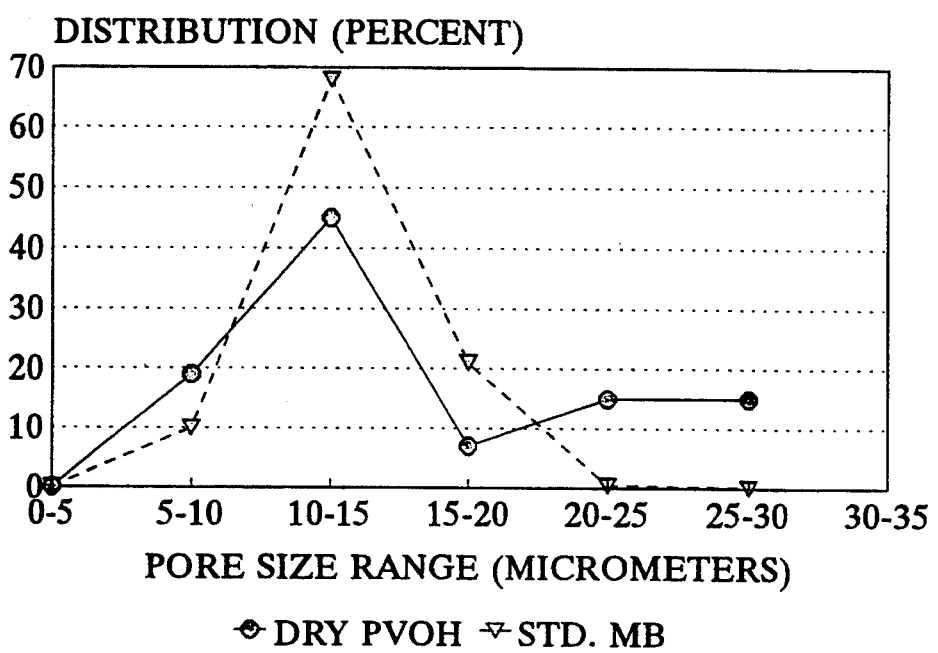
FIG. 2 is a plot of the pore size distribution of a porous, nonwoven liquid-activated barrier of the present invention in a dry state and a standard laminate commonly used as a barrier material.

The data for the "Dry" poly(vinyl alcohol) nonwoven web ("Dry PVOH") and the standard meltblown web ("STD. MB") were plotted in a similar fashion and are shown in FIG. 2. The two webs both have the largest number of pores in the 10–15 micrometer range, but otherwise are dissimilar. In particular, the poly(vinyl alcohol) nonwoven web has larger pores than does the meltblown web. Before being exposed to water, the maximum pore dimension of the former web was greater than 70 micrometers; after being exposed to water, the maximum pore dimension was reduced to about 43 micrometers.

Example 2

Preparation and Testing of Fluid-Activated Barrier

The procedure of Example 1 was repeated, except that the poly(vinyl alcohol) nonwoven web was formed directly on a polypropylene spunbonded nonwoven web to form a first bilayer laminate. The poly(vinyl alcohol) nonwoven web had a basis weight of 0.5 osy (about 17 gsm) and the spunbonded web had a basis weight of 0.7 osy (about 24 gsm). A preformed, second bilayer laminate consisting of a second polypropylene spunbonded nonwoven web having a basis weight of 0.7 osy (about 24 gsm) and a polypropylene meltblown nonwoven web having a basis weight of 0.5 osy (about 17 gsm) then was laid down on the first bilayer laminate. The meltblown nonwoven web was adjacent to and contiguous with the poly(vinyl alcohol) nonwoven web. The resulting laminate is referred to hereinafter as the Barrier laminate.

Two control laminates also were prepared. The first (Control A) consisted of a polypropylene meltblown nonwoven web sandwiched between two polypropylene spunbonded nonwoven webs. The basis weights of the meltblown web and each of the spunbonded webs were 0.5 osy (about 17 gsm) and 0.7 osy (about 24 gsm), respectively. The second (Control B) consisted of a laminate of two polypropylene meltblown nonwoven webs sandwiched between two polypropylene spunbonded nonwoven webs. Each of the meltblown webs had a basis weight of 0.5 osy (about 17 gsm) and each of the spunbonded webs had a basis weight of 0.7 osy (about 24 gsm).

The blood strike through characteristic of each laminate was measured as described in U.S. Pat. No. 5,213,881, which is incorporated herein by reference. The results after one minute and a pressure of 1 pound per square inch (psi, about 70 grams per square cm) are summarized in Table 2.

TABLE 2

Results of Blood Strike Through Measurements

| Laminate | Percent Strike Through |
|---|---|
| Barrier | 8.6 |
| Control A | 13.2 |
| Control B | 14.3 |

With a strike through of less than about 10 percent, the Barrier laminate clearly resulted in a significant reduction in blood strike through, even though no effort was made to optimize its properties, in comparison to laminates which are well known in the art for their impermeability to liquids.

Example 3

Evaluation of Swelling Behavior of Fiber Prepared from a Water-Swellable Polymer A solution of a water-swellable poly(vinyl alcohol), Airvol® 125, was prepared essentially as described in Example 1, except that fifteen parts of a mixture of the poly(vinyl alcohol) and PEG-400 in a ratio by weight of 9:1 were dissolved in 85 parts of de-ionized water.

Fibers were prepared by solution spinning the foregoing poly(vinyl alcohol) solution essentially as described in above-referenced U.S. patent application 08/172,018. In this instance, however, the bench-scale apparatus described therein was employed. Briefly, the apparatus consisted of a cylindrical steel reservoir having a capacity of about 60 cm³ and enclosed by an electrically heated steel jacket. A movable piston was located in one end of the reservoir and an extrusion die assembly, consisting of a manifold and a die tip, was connected to the other end. The die tip had a single extrusion orifice and was surrounded by the circular 0.075-inch (1.9-mm) gap of the manifold. The extrusion orifice had a diameter of 0.016 inch (0.41 mm) and a length of 0.060 inch (1.5 mm).

Extrusion of the poly(vinyl alcohol) solution was accomplished by the motion of the piston in the reservoir toward the die tip. The extruded threadline was surrounded and attenuated by a primary air stream exiting the circular gap. Attenuating air pressures typically were of the order of 0–8 psig. The wet threadlines then were dried by a secondary air stream which exited essentially normal to the threadline from another manifold. The secondary air stream manifold opening was about 5 cm from the threadline and about 5 cm below the die tip. The dried threadline was collected on a foraminous screen under which a vacuum box was located. The foraminous screen was 35–40 cm from the opening of the secondary air stream manifold.

Extrusion was carded out at about 70° C. The primary air stream was steam at a temperature of approximately 55° C. The secondary air stream was compressed air heated to a temperature of 260°–370° C. The exit velocities of the primary and secondary air streams were about 800 feet per second (about 244 meters per second) and 500 feet per second (about 152 meters per second), respectively.

The swelling behavior of the resulting fiber was evaluated by direct observation and video recording on a contrast-enhancing microscope, a Leitz Laborlux Pol microscope, set up for differential interference contrast (DIC) with a 40X DIC objective lens in accordance with the manufacturer's instructions. A standard VHS video system with an indexed frame counter was employed. The video system also recorded elapsed time. Dry fiber samples were mounted between a standard glass microscope slide and a No. 1½ cover slip. A drop or two of synthetic urine was placed at the edge of the cover slip and allowed to surround the fiber. Time zero was taken as the time when the fiber was surrounded by the synthetic urine. Video recording and 35-mm photographs were taken on the Leitz microscope.

The synthetic urine was prepared by adding 900 ml of distilled water to a 1,000-ml volumetric flask. The components of the synthetic urine, shown in Table 3, were added in the order listed in the table to avoid precipitating divalent cations because of the high pH of the solution. Each component was dissolved completely before adding the next one. When all of the components had been added, additional distilled water was added to bring the flask volume to 1,000 ml.

TABLE 3

| Synthetic Urine Composition | |
|---|---|
| Component | Amount, g |
| $KH_2PO_4$ | 0.681 |
| $Ca(H_2PO_4)_2.H_2O$ | 0.309 |
| $MgSO_4.7H_2O$ | 0.477 |
| $K_2SO_4$ | 1.333 |
| $Na_3PO_4.12H_2O$ | 1.244 |
| NaCl | 4.441 |
| KCl | 3.161 |
| $NaN_3$ | 0.400 |
| Urea ($NH_2CONH_2$) | 8.560 |
| Pluronic 10R8[a] | 0.100 |

[a] A wetting agent manufactured by BASF Corporation, Parsippany, New York.

The resulting videotape was played and fiber diameter measurements were made directly from the monitor at selected time intervals based on the recorded elapsed time. Also recorded was the diameter ratio, $D/D_0$. The results are summarized in Table 4; in the table, diameters are given in micrometers.

TABLE 4

| Summary of Fiber Swelling Behavior | | |
|---|---|---|
| Time, Sec. | Diameter | Diameter Ratio |
| 0.00 | 6.50 | 1.00 |
| 1.00 | 7.40 | 1.14 |
| 2.00 | 7.20 | 1.11 |
| 3.00 | 8.40 | 1.29 |
| 4.00 | 9.20 | 1.42 |
| 5.00 | 9.70 | 1.49 |
| 6.00 | 10.50 | 1.62 |
| 7.00 | 11.90 | 1.83 |
| 9.00 | 12.20 | 1.88 |
| 10.00 | 13.20 | 2.03 |
| 11.00 | 13.70 | 2.11 |
| 12.00 | 14.00 | 2.15 |
| 13.00 | 14.10 | 2.17 |
| 14.00 | 14.40 | 2.22 |
| 15.00 | 14.50 | 2.23 |
| 20.00 | 18.40 | 2.83 |
| 22.00 | 18.60 | 2.86 |
| 30.00 | 20.10 | 3.09 |
| 37.00 | 21.10 | 3.25 |
| 47.00 | 21.30 | 3.28 |
| 57.00 | 21.20 | 3.26 |
| 67.00 | 21.40 | 3.29 |
| 77.00 | 21.50 | 3.31 |
| 87.00 | 21.50 | 3.31 |

Figure 3:
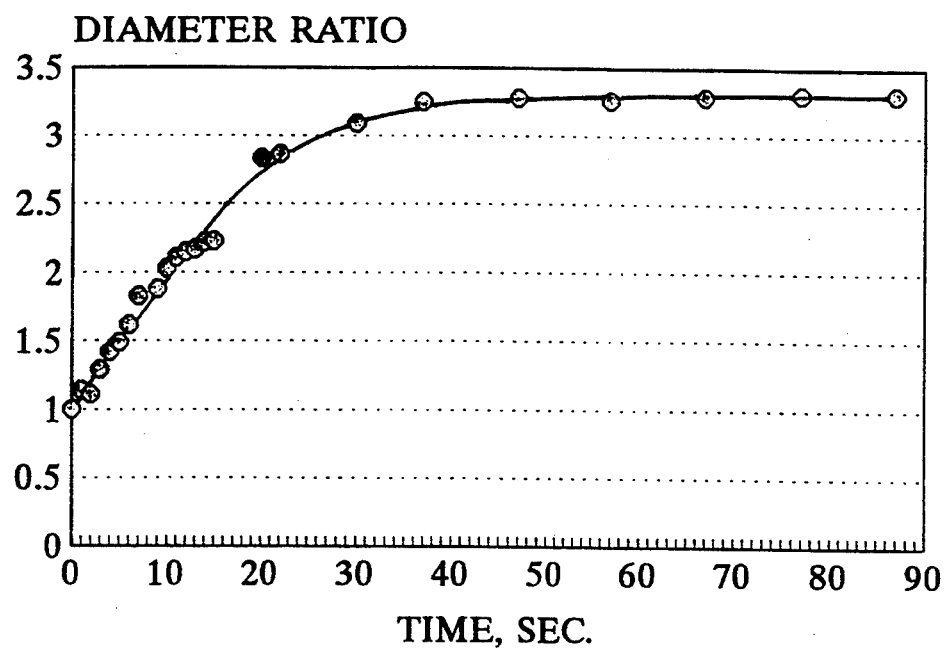
FIG. 3 is a plot of the ratio of the diameter of a fiber exposed to synthetic urine to the diameter of the fiber in the dry state versus time.

In order to more fully understand the swelling behavior of the fiber, the diameter ratio data of Table 4 were plotted versus time. Such plot is shown as FIG. 3. From the figure, it is evident that there was a rapid, essentially linear increase in the fiber diameter during about the first 15–20 seconds after exposure. Swelling subsequently was significantly slower and approached the maximum diameter ratio of about 3.3 which, as a practical matter, was reached roughly 40 seconds after exposure. A diameter ratio of 1.5 was achieved after about 5 seconds, and a diameter ratio of 2 was achieved after about 10 seconds. The diameter of the fiber tripled about 25 seconds after exposure.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto. For example, the porous, fibrous nonwoven web which comprises the porous, nonwoven liquid-activated barrier of the present invention can be composed of fibers composed solely of a liquid-swellable polymer. Alternatively, such fibers can be bicomponent fibers in which one component consists of a liquid-swellable polymer and the other component consists of a different polymer which is not swollen by a liquid. Examples of bicomponent fibers include, by way of illustration only, side-by-side fibers and sheath-core fibers. Bicomponent fibers also can be prepared from two different liquid-swellable fibers. Other variations and permutations will be readily apparent to those having ordinary skill in the art.

What is claimed is:

1. A porous, nonwoven liquid-activated barrier which comprises a porous, fibrous nonwoven web, in which:

at least about 50 percent by weight of the fibers comprising the fibrous nonwoven web are prepared from a liquid-swellable polymer which is not significantly soluble in the liquid;

the fibers have diameters in a range of from about 0.1 to about 100 micrometers;

the pores of the fibrous nonwoven web have a longest dimension in a range of from about 0.3 to about 300 micrometers; and in the presence of liquid, the fibers swell to an extent sufficient to substantially block the passage of liquid through the fibrous nonwoven web.

2. The porous, nonwoven liquid-activated barrier of claim 1 having a liquid strike through of less than about 10 percent.

3. A porous, nonwoven water-activated barrier which comprises a porous, fibrous nonwoven web in which:
   at least about 50 percent by weight of the fibers comprising the fibrous nonwoven web are prepared from a water-swellable polymer which is not significantly soluble in water;
   the fibers have diameters in a range of from about 0.1 to about 100 micrometers;
   the pores of the fibrous nonwoven web have a longest dimension in a range of from about 0.3 to about 300 micrometers; and
   in the presence of liquid, the fibers swell to an extent sufficient to substantially block the passage of liquid through the fibrous nonwoven web.

4. The porous, nonwoven liquid-activated barrier of claim 3 having a liquid strike through of less than about 10 percent.

5. The barrier of claim 3, in which at least about 70 percent by weight of the fibers comprising the fibrous nonwoven web are prepared from the water-swellable polymer.

6. The barrier of claim 3, in which substantially all of the fibers comprising the fibrous nonwoven web are prepared from the water-swellable polymer.

7. The barrier of claim 3, in which the water-swellable polymer is poly(vinyl alcohol).

8. The barrier of claim 7, in which the water-swellable polymer is not significantly soluble in water at a temperature less than about 50° C.

9. The barrier of claim 3, in which the fibers have diameters in a range of from about 0.5 to about 40 micrometers.

10. The barrier of claim 3, in which the pores of the fibrous nonwoven web have a longest dimension in a range of from about 2 to about 100 micrometers.

11. A porous, nonwoven water-activated barrier which comprises a multilayered nonwoven structure, at least one layer of which is a porous fibrous nonwoven web in which:
    at least about 50 percent by weight of the fibers comprising the fibrous nonwoven web are prepared from a water-swellable polymer which is not significantly soluble in water;
    the fibers of the fibrous nonwoven web have diameters in a range of from about 0.1 to about 100 micrometers;
    the pores of the fibrous nonwoven web have a longest dimension in a range of from about 0.3 to about 300 micrometers; and
    in the presence of liquid, the fibers swell to an extent sufficient to substantially block the passage of liquid through the fibrous nonwoven web.

12. The porous, nonwoven liquid-activated barrier of claim 11 having a liquid strike through of less than about 10 percent.

13. The barrier of claim 11, in which at least about 70 percent by weight of the fibers comprising the fibrous nonwoven web are prepared from the water-swellable polymer.

14. The barrier of claim 11, in which substantially all of the fibers comprising the fibrous nonwoven web are prepared from the water-swellable polymer.

15. The barrier of claim 11, in which the water-swellable polymer is poly(vinyl alcohol).

16. The barrier of claim 15, in which the water-swellable polymer is not significantly soluble in water at a temperature less than about 50° C.

17. The barrier of claim 11, in which the fibers of the fibrous nonwoven web have diameters in a range of from about 0.5 to about 40 micrometers.

18. The barrier of claim 11, in which the pores of the fibrous nonwoven web have a longest dimension in a range of from about 2 to about 100 micrometers.

19. A porous, nonwoven water-activated barrier which comprises:
    a first spunbonded nonwoven web;
    a porous, fibrous nonwoven web in which:
        at least about 50 percent by weight of the fibers comprising the fibrous nonwoven web are prepared from a water-swellable polymer which is not significantly soluble in water;
        the fibers of the fibrous nonwoven web have diameters in a range of from about 0.1 to about 100 micrometers;
        the pores of the fibrous nonwoven web have a longest dimension in a range of from about 0.3 to about 300 micrometers; and
        in the presence of liquid, the fibers swell to an extent sufficient to substantially block the passage of liquid through the fibrous nonwoven web.
    a meltblown nonwoven web having a first surface and a second surface; and
    a second spunbonded nonwoven web;
    in which the fibrous nonwoven web is adjacent to and contiguous with the first surface of the meltblown nonwoven web, the first spunbonded nonwoven web is adjacent to and contiguous with the fibrous nonwoven web, and the second spunbonded nonwoven web is adjacent to and contiguous with the second surface of the meltblown web.

20. The porous, nonwoven liquid-activated barrier of claim 19 having a liquid strike through of less than about 10 percent.

21. The barrier of claim 19, in which at least about 70 percent by weight of the fibers comprising the fibrous nonwoven web are prepared from the water-swellable polymer.

22. The barrier of claim 19, in which substantially all of the fibers comprising the fibrous nonwoven web are prepared from the water-swellable polymer.

23. The barrier of claim 19, in which the water-swellable polymer is poly(vinyl alcohol).

24. The barrier of claim 23, in which the water-swellable polymer is not significantly soluble in water at a temperature less than about 50° C.

25. The barrier of claim 19, in which the fibers of the fibrous nonwoven web have diameters in a range of from about 0.5 to about 40 micrometers.

26. The barrier of claim 19, in which the pores of the fibrous nonwoven web have a longest dimension in a range of from about 2 to about 100 micrometers.

27. The barrier of claim 19, in which each of the first and second spunbonded nonwoven webs and the meltblown nonwoven web is prepared from a polyolefin.

28. The barrier of claim 27, in which the polyolefin is polypropylene.

* * * * *